United States Patent [19]

Guess et al.

[11] 4,401,124
[45] Aug. 30, 1983

[54] REFLECTION ENHANCEMENT OF A BIOPSY NEEDLE

[75] Inventors: Joe F. Guess; Dennis R. Dietz, both of Littleton; Charles F. Hottinger, Englewood, all of Colo.

[73] Assignee: Technicare Corporation, Solon, Ohio

[21] Appl. No.: 292,470

[22] Filed: Aug. 13, 1981

[51] Int. Cl.³ .............................................. A61B 10/00
[52] U.S. Cl. ................................... 128/660; 128/753; 128/754
[58] Field of Search ................. 73/603, 604, 605, 642, 73/644; 128/660, 753, 754

[56] References Cited

U.S. PATENT DOCUMENTS 4,058,114 11/1977 Soldner ................................ 128/660
4,207,901 6/1980 Nigam .................................. 128/660
4,249,539 2/1981 Vilkomerson ....................... 128/660

FOREIGN PATENT DOCUMENTS 25214 3/1981 European Pat. Off. ............ 128/660
2919024 7/1980 Fed. Rep. of Germany ...... 128/660
2318420 2/1977 France ................................ 128/660

Primary Examiner—Richard J. Apley
Assistant Examiner—George Yanulis
Attorney, Agent, or Firm—Audley A. Ciamporcero, Jr.; W. Brinton Yorks, Jr.

[57] ABSTRACT

Method and apparatus for enhancing the reflection coefficient of a surgical instrument for use in conjunction with an apparatus for pulse-echo ultrasound imaging of an area of the body, by means of a diffraction grating disposed on the surgical instrument.

14 Claims, 4 Drawing Figures

REFLECTION ENHANCEMENT OF A BIOPSY NEEDLE

BACKGROUND OF THE INVENTION

Ultrasonic pulse-echo imaging systems are seeing increasing use in surgical procedures involving the insertion of a surgical instrument into the body for both the diagnosis and treatment of the body. One such procedure involves the obtaining of tissue samples by vacuum aspiration of the tissue through a hollow needle inserted into the body. Considerable efforts have been expended to provide accurate means for monitoring of the inserted instrument to avoid inadvertent tissue or organ puncture.

U.S. Pat. No. 4,249,539 outlines some of the difficulties encountered in monitoring the tip of the vacuum aspiration needles by use of either ultrasonic pulse-echo imaging or x-ray imaging. The solution proposed by U.S. Pat. No. 4,249,539 is the use of a second omnidirectional transducer at the tip of the needle or needle insert. Such a solution requires costly and complex electronics to be built into the needle or the needle insert. In addition, such a needle or needle insert cannot be autoclaved.

U.S. Pat. Nos. 3,556,079; 4,058,114; 4,029,084; and 3,721,227, involving method and apparatus for imaging the tip of an inserted needle or surgical instrument, may be fairly characterized as imposing highly restricted directional limitations on the inroduction of the needle or surgical instrument, whereby uncertainty and inaccuracy results. U.S. Pat. No. 3,556,079 discloses a method wherein organs or vessels which are in motion are irradiated and the backscattered waves exhibit a Doppler shift due to the motion of the organ or vessel.

This method has many drawbacks. In the method as depicted in FIG. 8a, the needle with transducer must be inserted in a direction such that it will encounter the anticipated Doppler shift to receive guidance in insertion. In the method depicted in FIGS. 8b and 8c, an external transducer as well as a transducer in the inserted needle must be disposed with respect to one another that the needle or the external transducer respectively encounters the anticipated Doppler shift.

U.S. Pat. Nos. 3,721,227 4,029,084; and 4,108,165 disclose systems wherein the first external transducer surrounds or encloses an opening through which a needle or surgical instrument may be directed and, which systems are therefor limited to the A-mode scanning technique which is not the preferred diagnostic approach due to the relatively small information content of its output.

U.S. Pat. No. 4,058,114 discloses an apparatus wherein the angle of insertion of the needle is disclosed by the external mechanical coupling for the needle; and an aiming pin disposed at the same angle as the external mechanical coupling of the needle overlies the visual picture of the ultrasound system providing only an imaginary overlay of the mechanical indicator and the electronic display.

U.S. Pat. No. 4,219,886 discloses a multipoint reflective target system for use as sonar targets. With the proper selection of the length of the sonar pulse, the spacing of the reflectors, and the size and material of the reflectors, the multipoint reflective target system can be made to resemble much larger, actual or simulated targets.

SUMMARY OF THE INVENTION

The present invention involves both method and apparatus for performing surgical procedures using an ultrasound pulse-echo imaging system, and provides a simple, effective and inexpensive means for enhancing the reflection coefficient of the surgical instrument means inserted within the body by use of a diffraction grating disposed on a surface of the surgical instrument means. The diffraction grating comprises a multiplicity of substantially parallel grooves. The distance between the depth of adjacent grooves being defined as follows:

$$D = \frac{N \lambda o}{2 \cos \theta}$$

where N is an integer, $\lambda o$ is a center wavelength of the transducer of the ultrasound imaging system and $\theta$ is equal to the angle between the incident beam and a line along the surface of the instrument and perpendicular to said grooves. In a preferred embodiment, the surgical instrument comprises a hollow needle. The grooves on said hollow needle may be formed so as to extend about the circumference thereof in a helical pattern. In a still preferred embodiment, the tip of the needle has a diameter of 0.1 inches and the grooves have a depth of 0.005 inches. The diffraction grating may not only be disposed on the tip of an inserted needle or surgical object to monitor the insertion. thereof but may also be disposed on that portion of an object within the body, the position of which is to be monitored.

DETAILED DESCRIPTION OF THE INVENTION

Figure 1:
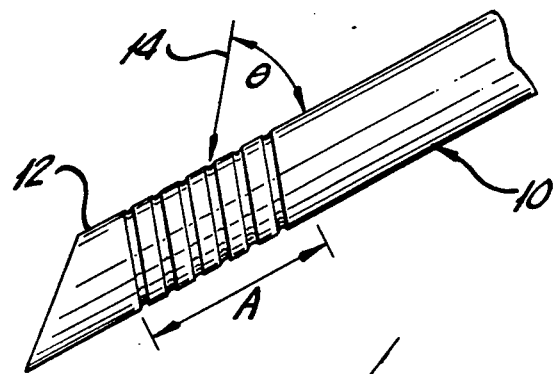
FIG. 1 is a perspective view of a preferred embodiment of a surgical instrument means according to the present invention.

FIG. 1 illustrates a preferred embodiment of the surgical instrument means of the present invention for use in conjunction with the apparatus and method for performing surgical procedures according to the present invention. The surgical instrument means 10 comprises a hollow needle which may be used, for example, in vacuum aspiration of tissue samples. The tip 12 of the needle has a groove defining a diffraction grating disposed along a surface A thereof. As used herein, "diffraction grating" shall mean a system of bars, lines, bands, or grooves on an otherwise substantially smooth surface which reflects or scatters incident energy. In accordance with the principles of the present invention, the component lines/grooves of a diffraction grating are selected in conjunction with signal characteristics such that construction reinforcement occurs along the axis of incident energy, thereby enhancing signal received at the ultrasound transceiver. The diffraction grating on the tip of the needle enhances the reflection coefficient of the tip or leading edge of the hollow needle.

Figure 2:
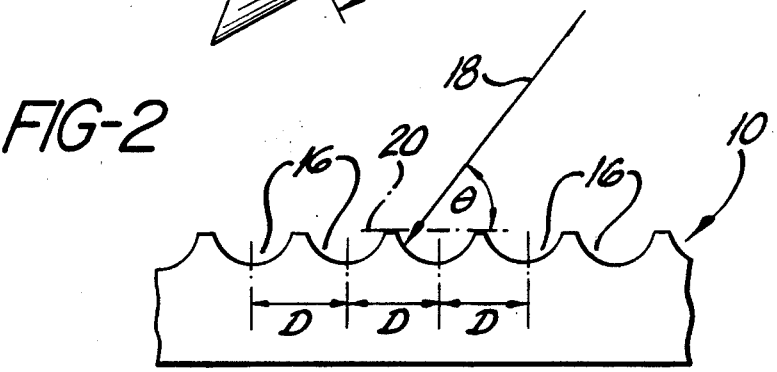
FIG. 2 is an enlarged side view of surface A of the surgical instrument means of FIG. 1.

The hollow needle may be used in conjunction with an apparatus for performing surgical procedures comprising a pulse-echo ultrasound imaging system including a transducer means adapted to be accoustically coupled to the exterior of the body. Ultrasonic beams 14 incident on the diffraction grating are reflected and scattered, thereby providing an enhanced reflection coefficient of the surface A of the tip of the needle. Though the preferred embodiment of FIG. 1 shows the diffraction grating located at the tip or leading edge of a hollow needle, the present invention also encompasses the provision and use of a diffraction grating at the leading edge of any surgical instrument for insertion within the body, or along any surface of an object to be monitored while in the body. It should also be noted that a diffraction grating may be located on a removable insert for a hollow needle. In the method of the present invention, the diffraction grating means may be used to provide an enhanced coefficient of reflection of the leading edge of an instrument, or a portion of an object to aid in monitoring the insertion of a surgical instrument into the body or monitoring of the position of an object within the body FIG. 2 shows an enlarged side view of surface A of the surgical instrument means of FIG. 1. The diffraction grating shown comprises a multiplicity of substantially parallel grooves 16 disposed perpendicular to the length of the instrument. The distance between the depth of adjacent grooves may be defined as follows:

$$D = \frac{N \lambda o}{2 \cos \theta}$$

where N is an integer, $\lambda o$ is the center wavelength of the exterior transducer of the ultrasound pulse-echo imaging system (not shown) and $\theta$ is equal to the angle between the incident beam 18 and a line 20, along the surface A and perpendicular to the grooves. So spaced, the grooves provide constructive interference of the scattered and reflected beam yielding maximum reflection back along the line of the incident beam. A given diffraction grating will yield an enhanced reflection over a range of angles surrounding $\theta o$ which range is determined by the band width of the external transducer of the ultrasound pulse-echo imaging system.

It may be seen that though D of the diffraction grating may be selected according to a given most probable angle of insertion or use of the surgical instrument or object, the actual angle of insertion or use may vary from said angle by a significant range and the diffraction grating will still give enhanced reflection. It should be noted that range of angles allows movement of the transducer as well as movement of the diffraction grating. If this range is insufficient, a second diffraction grating of the required D may be used. This second grating may be provided on a second surgical instrument or object, or may be provided along side the first diffraction grating on the same surgical instrument or object.

Figure 3:
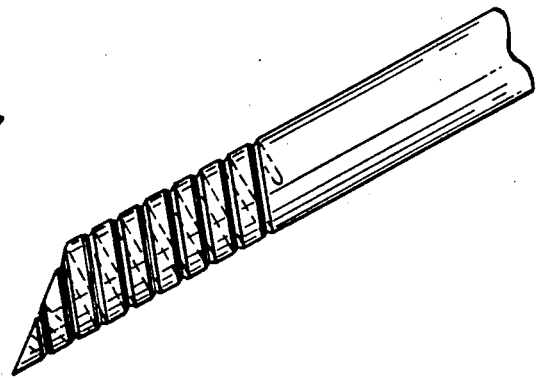
FIG. 3 is a perspective view of a still preferred embodiment of the surgical instrument means of the present invention.

FIG. 3 is an illustration of a still preferred embodiment of the surgical instrument means of the present invention comprising a hollow needle showing a multiplicity of substantially parallel grooves disposed along the tip thereof. The grooves in actuality extend about the circumference of the tip in a helical pattern, forming a continuous diffraction grating about the tip of the needle.

Figure 4:
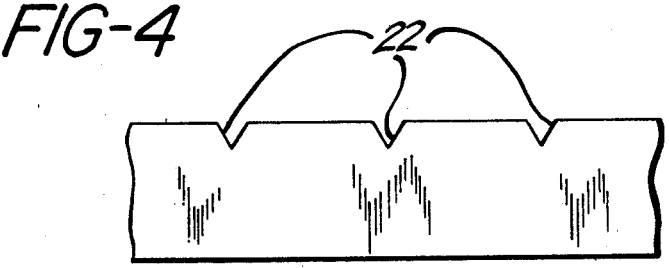
FIG. 4 is a side view of the diffraction grating of an alternative embodiment of the surgical instrument means of the present invention.

FIG. 4 illustrates an alternative embodiment of the surgical instrument means of the present invention, with a diffraction grating comprising grooves 22. According to the present invention the grooves may be of any cross-sectional shape and the remaining width of the surface A between the grooves is not specified. Grooves of semi-circular cross-section are easily formed, and in the most preferred embodiment of the present invention, such as a hollow needle shown in FIG. 3, the needle tip has a diameter of 0.1 inches, and a helical pattern of semi-circular grooves having a depth of 0.005 inches.

The foregoing description of the drawings is illustrative and is not to be taken as limiting, still other variations and modifications are possible without departing from the spirit and scope of the present invention.

We claim:

1. Apparatus for performing surgical procedures upon select, internal body tissues, comprising:
    (a) a pulse-echo ultrasound imaging system for imaging the area of the body including said tissues, said imaging system including transducer means adapted to be accoustically coupled to the exterior of the body; and
    (b) surgical instrument means for insertion into the body for performing said surgical procedures, said surgical instrument means having a surface A comprising a diffraction grating for enhancing the reflection coefficient of the surgical instrument means.

2. An apparatus as in claim 1 wherein said diffraction grating comprising a multiplicity of substantially parallel grooves disposed substantially perpendicular to the length of the instrument means, the distance between the depths of adjacent grooves being defined as follows:

$$D = \frac{N \lambda o}{2 \cos \theta}$$

where N is an integer, $\lambda o$ is the center wavelength of the transducer and $\theta$ is equal to the angle between the incident beam and a line along the surface A and perpendicular to the grooves.

3. An apparatus as in claim 1 or 2 wherein said surgical instrument means comprises a hollow needle.

4. An apparatus as in claim 3 wherein the grooves on said hollow needle extend around the circumference thereof and form a helical pattern.

5. An apparatus as in claim 3 where the tip of the needle has a diameter of 0.1 inches and the depth of the grooves is 0.005 inches.

6. A surgical instrument for insertion into the body and used in conjunction with a pulse-echo ultrasound imaging system for performing surgical procedures, said imaging system including a transducer adapted to direct an incident beam of a given wavelength into the body, and said surgical instrument comprising:
    a leading edge having a surface including a diffraction grating for enhancing the reflection coefficient of the leading edge of the surgical instrument.

7. A surgical instrument as in claim 6 wherein said diffraction grating comprising a multiplicity of substantially parallel grooves disposed substantially perpendicular to the length of the instrument means, the distance between the depths of adjacent grooves being defined as follows:

$$D = \frac{N\lambda_o}{2\cos\theta}$$

where N is an integer, $\lambda_o$ is the center wavelength of the transducer and $\theta$ is equal to the angle between the incident beam and a line along the surface A and perpendicular to the grooves.

8. A surgical instrument as in claim 7 wherein said surgical instrument comprises a hollow needle.

9. A surgical instrument as in claim 8 wherein the grooves on said hollow needle extend around the circumference thereof and form a helical pattern.

10. A surgical instrument as in claim 8 where the tip of the needle has a diameter of 0.1 inches and the depth of the grooves is 0.005 inches.

11. In a surgical procedure, a method of monitoring an object within the body, said object including a diffraction grating, and the method comprising the steps of:
  (a) irradiating a body area utilizing pulse-echo ultrasound techniques;
  (b) inserting said object into said body area; and
  (c) producing an image of said body area, including the enhanced reflection of the diffraction grating of the object.

12. In a surgical procedure, a method of monitoring an object within the body, said object including a diffraction grating on a surface A of said object to enhance the reflection coefficient thereof, said diffraction grating comprising a multiplicity of substantially parallel grooves, the distance between the depth of adjacent grooves being defined as follows:

$$D = \frac{N\lambda_o}{2\cos\theta}$$

where N is an integer, $\theta$ is equal to the angle between an incident ultrasound beam of center wavelength $\lambda_o$ and a line along surface A and perpendicular to said grooves; the method comprising the steps of:
  (a) irradiating a body area utilizing pulse-echo ultrasound techniques with an ultrasound beam of center wavelength $\lambda_o$;
  (b) inserting said object into said body area; and
  (c) producing an image of said body area, including the enhanced reflection of the diffraction grating of the object.

13. The surgical procedure of claim 11, wherein said object comprises a surgical instrument.

14. The surgical procedure of claim 12, wherein said object comprises a surgical instrument.

* * * * *